United States Patent [19]

Narasimhan et al.

[11] 4,288,546
[45] Sep. 8, 1981

[54] PROCESS FOR THE LARGE SCALE PRODUCTION OF PITUITARY HORMONES BY SERIAL SECONDARY SUSPENSION CULTURE

[75] Inventors: Mandayam J. Narasimhan, Mysore, India; John A. Anderson, Menlo Park, Calif.

[73] Assignee: The Regents of the University of Minnesota, Minneapolis, Minn.

[21] Appl. No.: 957,725

[22] Filed: Nov. 6, 1978

Related U.S. Application Data

[63] Continuation-in-part of Ser. No. 675,643, Apr. 9, 1976, Pat. No. 4,124,448.

[51] Int. Cl.$^2$ .......................... A01N 1/02; C12P 21/02; C12N 5/02
[52] U.S. Cl. ...................................... 435/70; 435/241; 435/948
[58] Field of Search ...................... 195/1.8; 435/2, 70, 435/241

[56] References Cited

U.S. PATENT DOCUMENTS 3,073,746  1/1963  Thompson et al. ................ 195/1.8

OTHER PUBLICATIONS

The Merck Index–ninth edition (1976) p. 7290.
Betteridge et al.–Chem. Abst. vol. 80 (1974) p. 44148 K.

*Primary Examiner*—Frederick E. Waddell
*Attorney, Agent, or Firm*—Burd, Bartz & Gutenkauf

[57] ABSTRACT

A new system of serially culturing anterior pituitary gland cells in a new nutrient medium under open aeration to produce large amounts of pituitary hormones. Using the new system of culture and new nutrient media, the pituitary cells can be grown in vitro to produce in approximately three weeks 10 to 12 times the amount of extractable hormone originally present in the original tissue.

4 Claims, No Drawings

PROCESS FOR THE LARGE SCALE PRODUCTION OF PITUITARY HORMONES BY SERIAL SECONDARY SUSPENSION CULTURE

This application is a continuation-in-part of our copending application Ser. No. 675,643, filed Apr. 9, 1976, now U.S. Pat. No. 4,124,448, issued Nov. 7, 1978.

BACKGROUND OF THE INVENTION

This invention pertains to the field of medicine and medical biology. The specific sub-area of medicine and medical biology is the art of the in vitro culture of mammalian tissue cells. Many nutrient culture mediums have been developed and are, to a large extent, specifically designed to permit prolonged and sustained growth of specific types of cells, such as those derived from skin, from tumors, and from various other tissues in mammalian species. These are grown by primary culture systems as explants, monolayers or suspension cultures or secondary cell lines. However, there is no culture system or nutrient media available at the present which will permit prolonged growth and proliferation of human anterior pituitary cells in sufficient number to provide a source of large amounts of growth hormone and other pituitary hormones. This lack of success is related to many factors, among which are (1) limited knowledge concerning the specific nutrients for the specific cells, (2) the general trend for the pituitary hormone-producing cells to lose their function of producing hormones, (3) death of cells after a few days to a few weeks, and (4) transformation of cells to non-functioning fibroblastic or fibroblastoid type cells.

Some of the previous studies which indicate the difficulties encountered are as follows: Animal and human pituitary cells have been maintained as explants in cultures and are known to release their hormones for variable periods of time. Continuous cell lines derived from induced tumors in rats may proliferate for several weeks or a few months and are able to secrete some amounts of rat growth hormone. (Takemoto, H., Yokoro, K., Furth, J. and Cohen, A. I., Cancer Res., 22:917–924, 1962; Tashjian, A. H. and Hoyt, R. F., Jr., *In Molecular Genetics and Developmental Biology*, edited by M. Sussman, pp. 353-387, Prentice-Hall, New Jersey, 1972). Tumors of the human pituitary gland have also been maintained in culture and may secrete human growth hormone into the culture media for variable periods of time (Kohler, P. O., Bridson, W. E., Rayford, P. L. and Kahler, S. E., Metabolism, 18:782, 1969; Batzdorf, U., Gold, V., Matthews, N. and Brown, J., *Neurosurgery* 34:741, 1971; Peillon, F., Gourmelen, M., Donnadieu, M., Brandi, A., Sevaux, D. and Pham Huu Trung, M. T., Acta Endocrinol., 79:217–229, 1975) whereas normal human pituitary cells in culture survive and produce hormone only for a relatively brief period of time. The number of cells and the amount of hormone produced in such systems decline rapidly with time (Vidal-Tixier, A., Gourdji, D. and Tougard, C., Intern. Rev. Cytol., 41:173–239, 1975). Human fetal pituitary cells secreting growth hormone have also been cultured for several days but ultimately die or are transformed into fibroblast type cells (Gailani, S. D., Nussbaum, A., McDougall, W. J. and McLimans, W. F., Proc. Soc. Exp. Biol. and Med., 134:27–32, 1970).

The above described previously reported results by others were obtained by a culture procedure in which either small explanted pieces of tissue or a monolayer of cells were grown in small volumes in medium (Peillon et al, Vidal-Tixier et al and Gailani et al, cited above), into which only a small amount of growth hormone was released or secreted by the cells. The nutrient mediums used in these cultures have been unable to permit replication of the growth hormone producing cells. In all of these previously reported studies, the rate of cell multiplication and the amount of hormone produced, while persisting for a brief period of time, rather rapidly declines (Peillon et al). The culture systems or media used did not adequately meet the growth and metabolic needs of the cells as conversion to fibroblastoid cells, which are non-hormone producing or a loss of the growth hormone synthesis capacity in the cells or death of the cells occurred.

The literature concerning the art of tissue culture procedure and of nutrient medium developed is very voluminous and particularly extensive over the last 20 to 25 years. The hormones produced by the anterior pituitary in man include human growth hormone, ACTH (adrenocorticotrophic hormone), LH (lutenizing hormone), FSH (follicle stimulating hormone), PRL or LTH (prolactin or luteotrophic hormone) and TSH (thyrotrophic hormone). The inventors have been unable to find evidence of a previously described culture system or nutrient medium which permits the growth and proliferation of human pituitary hormone producing cells in sufficient amounts and over a long period of time to produce adequate amounts of hormone which can be biochemically extracted and used to treat hormone deficient states in man.

SUMMARY OF THE INVENTION

Broadly stated, the invention comprises a process involving a new culture system and new culture media for growing in vitro normal human or other animal pituitary cells for producing large amounts of pituitary hormones, human growth hormone, human ACTH, LH, FSH, PRL or LTH and TSH, and corresponding pituitary hormones of other animal species. More specifically, the invention comprises a process for producing pituitary hormone in which cells of the human or other animal anterior pituitary gland are dispersed in an amino acid-rich nutrient medium supplemented with liver extract, insulin and other peripheral hormones and anti-bacterial and anti-fungal agents and incubated under open-aeration cell growth conditions. The resulting culture is serially sub-cultured several times until the optimum desired cell growth level is achieved. The hormone is extracted from the cells using conventional techniques.

DETAILED DESCRIPTION OF THE INVENTION

An exemplary nutrient medium rich in amino acids is that known as Medium 199-1X with Earle's modified salts (Proc. Soc. Exp. Biol Med., 73:1, 1950, Growth, 15:11, 1951, Proc. Soc. Exp. Biol. Med., 74:22, 1950; Proc. Soc. Exp. Biol. Med., 73:880, 1951; J. Cell & Comp. Physiol., 36:411, 1950; J. Am. Med. Assn., 151:1081, 1953). To each liter of medium there is added from about 5 to 20 ml of liver extract, preferably about 10 ml; about 6 to 20 International Units of insulin, preferably about 10 I.U.; and minor amounts of anti-bacterial and anti-fungal anti-biotics.

As disclosed in our copending U.S. Pat. No. 4,124,448 preferred nutrient composition (Medium Beta) for producing growth hormone according to the present invention is as follows:

(1) Medium 199-1X with Earle's Modified Salts, GIBCO (Grand Island Biological Company), 1000 ml.
(2) Liver extract containing B vitamins (Lexavite Injectable, Eli Lilly and Company), 10 ml.
(3) Insulin, Crystalline, 10 International Units.
(4) Crystalline Sodium Penicillin G, 500,000 units.
(5) Streptomycin Sulfate, 500 mg.
(6) Nystatin, a polyene anti-fungal anti-biotic, 50,000 units.

The insulin should not be added to the medium until time of use because insulin will degrade in the medium between 4 and 8 days, particularly when kept at room temperature or above.

Although the anterior pituitary hormones ACTH, TSH, FSH, LH and Prolactin can be obtained by culturing serially human pituitary cells in Medium Beta used for the serial culture of pituitary cells to make human growth hormone, for optimum production of each of these hormones an additive is included in the medium as follows: to produce ACTH, a small amount of hydrocortisone or other corticosteroid or other substances with cortisone-cortisol-like activity, such as prednisolone, prednisone, triamcinolone, beta-methasone, para-methasone, dexa-methasone, fluorocortisol, and the like; to produce FSH, a small amount of estrogen or other comparable estrogens or non-steroidal estrogens or substances with estrogenic activity, such as natural estrogens including estradiol, estrone and estriol and synthetic estrogens including diethylstilbestrol, hexestrol, benzestrol, dienestrol, promethestrol, ethinylestradiol, or the like; to produce LH and Prolactin, a small amount of an estrogenic material and progesteron or other progesterons or progestational substances or compounds with progesteron androgenic activity such as natural progesterone, medroxy progesterone, ethinyltestosterone, hydroxy progesterone, norethyndrone, norethynodrel, ethynodiol-diacetate, dydrogesterone, chlormadinone, dimethisterone, ethinylestrenol, fluoro-medroxy progesterone, and the like; to produce Prolactin, a small amount of a progesteron-androgenic material; and to produce TSH, a small amount of levothyroxin or related natural material such as sterile thyroid powder, triiodothyronine and thyroglobulin, and synthetic or semi-synthetic thyroxin, such as synthetic sodium levothyroxine, sodium liothyronine, or the like. Examples of such specialized mediums include the following:

Medium Beta Hc for culturing pituitary cells to produce ACTH:
Medium 199 with Earle's base—100 ml
Lexavite (Injec. Liver Extr.)—1 ml
Crystalline Insulin—1.5 Units
Penicillin Na—50,000 Units
Streptomycin Sulphate—50 mg
Nystatin—5000 Units
Hydrocortisone Na succinate—1.25 mgs (0.625 to 2.5 mg Medium Sigma for culturing pituitary cells to produce FSH and LH:
Medium 199 with Earle's base—100 ml
Lexavite (Injec. Liver Extr)—1 ml
Crystalline Insulin—1.5 Units
Penicillin Na—50,000 Units
Streptomycin sulphate—50 mg
Nystatin—5000 Units
Aqueous suspension of estrogen (Estradiol monobenzoate—1 mg (0.5 to 3 mg)

Medium Sigma Pi for culturing pituitary cells to produce LH and Prolactin:
Medium 199 with Earle's base—100 ml
Lexavite (Injec. Liver Extr)—1 ml
Crystalline Insulin—1.5 Units
Pencillin Na—50,000 Units
Streptomycin sulphate—50 mg
Nystatin—5000 Units
Aqueous suspension of estrogen (Estradiol monobenzoate—1 mg (0.5 to 5 mg)
Soluble progesteron (Medroxyprogesteron)—5 mg (1 to 10 mg)

Medium Pi for culturing pituitary cells to produce Prolactin:
Medium 199 with Earle's base—100 ml
Lexavite (Injec. Liver Extr)—1 ml
Crystalline Insulin—1.5 Units
Penicillin Na—50,000 Units
Streptomycin sulphate—50 mg
Nystatin—5000 Units
Soluble progesteron (Medroxyprogesteron)—5 mg (1 to 10 mg)

Medium Theta for culturing pituitary cells to produce TSH:
Medium 199 with Earle's base—100 ml
Lexavite (Injec. Liver Extr)—1 ml
Crystalline Insulin—1.5 Units
Penicillin Na—50,000 Units
Streptomycin sulphate—50 mg
Nystatin—5000 Units
Levothyroxin—10 microgms. (5 to 20 $\mu$g)

To achieve sustained growth and proliferation of anterior pituitary cells and obtain a large volume of media to extract large amounts of pituitary hormones, a novel modified system of culturing is used. This involves the growing of dispersed cells of the human anterior pituitary in containers containing one of our new mediums with an open-aeration system for a period of several days, preferably about 8 days, followed by serial subculturing about every 4 to 8 days. The cultures may be grown as still-suspension cultures or as rotary suspension cultures. The technique involves greater degreees of aeration than is presently employed in culturing of human and mammalian cells. This is achieved by having open air vent caps on the containers which are placed in a 37° C. incubator with water troughs for moisture, provided with an air-flow system of about 8 to 16 liters of sterile air per minute. Addition of 5% $CO_2$ to the air-flow which is usually employed in presently available tissue culture techniques is avoided since we have found that human pituitary cells do not grow well and do not produce hormones in the presence of 5% $CO_2$.

Following about 8 days growth the cultures are subcultured serially, utilizing an appropriate dilution range of 1 volume of medium containing cells added to 1 volume of fresh medium. The original culture may be divided into 2, 3 or more parts, depending upon the cell growth found at each sub-culture time. If cell numbers are large by microscopic examination, greater sub-culture dilution transfers should be employed. If cells are fewer in number, less dilution transfers of medium containing cells to fresh medium should be used. Cultures should be protected from bacterial, fungal and viral contamination at all times.

The invention is further illustrated by the following examples:

EXAMPLE 1

Using the preferred Medium Beta nutrient composition described above, an initial tissue inoculum (about ⅓ of an anterior pituitary gland) was grown in serial culture with ½ volume transfers every 8 days for 32 days. The following average concentrations of hGH in ng/ml found in the medium were: at 8 days 21,166; at 16 days 18,666; at 24 days 21,750; and at 32 days 20,000. Each culture flask contained 30 ml and hence because of one-half dilutions and volume reconstitution at sub-culture times, the total amount of hGH produced at each sub-culture time was as follows: 8 days 5.01 mg in 6 flasks; at 16 days 6.7 mg in 12 flasks; at 24 days 15.6 mg in 24 flasks; and, by 32 days 28 mg in 48 flasks. Cultures have been grown for as long as two months. Preliminary characterization studies utilizing a Sephadex gel filtration procedure indicate that 80 to 90% of the immune reacting hGH is a monomer. Cells were epithelial in type, 10–14$\mu$ in diameter, contained chromatin granules and a large highly chromatic nucleus. Mitosis was present.

EXAMPLE 2

Following the procedure of Example 1, but using Medium Beta Hc, ACTH was obtained in the range of 3,000 to 10,000 picograms per ml of medium, with an average value of 4,000 picograms per ml. By the 32nd day of serial sub-culturing an estimated value of 5,760,000 picograms or 5.7 micrograms was obtained.

EXAMPLE 3

Similarly, following the procedure of Example 1, but using Medium Sigma, FSH was obtained in the range of 700 to 750 milli-International Units/ml. By the 32nd day of serial sub-culturing an estimated value of 1,080 International Units was obtained. LH is produced in the range of 1,600 to 2,000 milli-International Units/ml. By the 32nd day of serial subculturing one obtains an estimated amount of 230.4 International Units.

EXAMPLE 4

In the same manner, using Medium Pi, PRL is produced in the range of 100 to 250 ng/ml. By the 32nd day an estimated amount of 288 mgs is produced.

EXAMPLE 5

Using Medium Theta according to the same procedure, TSH is produced in a range of 300 to 500 microunits/ml. By the 32nd day an estimated amount of 576,000 microunits or 576 Units of TSH is produced.

By this new technique of serial sub-culture, one is able to obtain a large mass of pituitary cells for producing large amounts of growth hormone, ACTH, LH, FSH, PRL or TSH in relatively short periods of time.

The effectiveness of the medium resides in the addition of certain of the medium components which have not heretofore been utilized. The medium avoids the early death of cells as compared with previous culture mediums that have been used. The pituitary cells are able to incorporate radioactive labeled thymidine which is an evidence of cell growth and proliferation. The medium also prevents the growth or formation of fibroblasts or the conversion of the anterior pituitary cells into a fibro-blastic type cell. Fibroblastic transformation is a common problem with presently available tissue culture systems. The medium permits cell growth and multiplication as is evident by mitotic activity within the cells, and an increase in cell mass about every 8 days of cells which continue to be capable of continuing production of growth hormone. This has been repeatedly confirmed by radioimmune assays for human growth hormone, ACTH, LH, FSH, PRL and TSH at every sub-culture done to increase the number of flasks with cells producing these hormones. We have found that human growth hormone undergoes a degradation of 50% every three days in the medium used for their growth and proliferation. In spite of such a concommitant degradation, we have been able to obtain large amounts of human growth hormone by this new culture technique utilizing our new media.

There is a great need to produce human anterior pituitary growth hormone as it is, at present, in high demand. At present human growth hormone is prepared by a process of direct extraction of growth hormone from fresh pituitary glands obtained from humans at autopsy. The amount of human growth hormone that can be produced by this method is very small. The supply now available is but a fraction of the amount needed to treat human infants and children with growth hormone deficiencies. Previously pituitary growth hormones were extracted from animal pituitary glands (sheep, beef, pig and even fish) and were used to treat human subjects. Treatment trials about 20 years ago with these hormones resulted in failure because animal growth hormones were a foreign type of protein which produced neutralizing and sensitizing antibodies in the patients, rendering the animal growth hormone ineffective and allergenic. It is now known that only the molecular species of human growth hormone obtained from human pituitaries can be used in human subjects.

The distinct advantages of the medium, when used in an appropriate culture procedure, are as follows: One whole human pituitary gland provides about 2 to 4 milligrams of extractable human growth hormone. Utilizing the above medium and starting with a small single inoculum of about one-third of a human anterior pituitary gland which contains approximately 1.5 milligrams of extractable growth hormone, as the initial cell culture inoculum, one achieves 5 milligrams available in the media within 8 days, approximately 6 milligrams by 16 days, approximately 30 milligrams by 32 days, and so on, utilizing a serial dilution sub-culture procedure and the herein-defined nutrient media. Hence, this process of culturing of pituitary cells provides an amount of growth hormone available in the medium for extraction and purification that is approximately 20 times more than that present in the initial pituitary tissue which was used as the seed culture in a period of 32 days. Since there is a concommitant degradation of 50% of the growth hormone in the media every three days, these values represent human growth hormone produced above and beyond that degraded concommitantly.

The process of the present invention is adaptable to continuous or intermittent flow fermentation. Modifications of our present harvesting system by the use of appropriate filters to collect only the media at shorter intervals than 4 to 8 days, followed by recycling of the media after extraction of the secreted growth hormone by a continuous fermentation process would enable one to produce larger amounts of growth hormone.

Our experiments have confirmed that the growth hormone extracted and purified from our process of tissue culture is biologically active, using the presently available bioassays. It has a bioactivity of 2 to 2.2 units per mg of immunoreactivity which is the optimum bioactivity seen with human growth hormones available at present. Another advantage of a tissue culture procedure for production of human growth hormone is that at least 80 to 90% of the human growth hormone is in the monomer form, the simple physiologically active form. Direct extraction of growth hormones from human pituitary glands provides, in addition to monomer, dimers and polymers; the two latter are thought to be antigenic in human subjects. Most human growth hormones available today contain monomers, dimers, polymers (approximately one-third) each), the growth hormone from the Scandinavian agencies (NIL-Denmark, KABI-Sweden), being better in terms of a purer monomer content than the growth hormone made by the U.S. National Pituitary Agency. It is interesting to note that the growth hormone made by our process, because of its almost pure monomeric content, is far superior to those currently available in the United States.

At present the cost of treatment of one child with a growth hormone deficiency is very high. Such treatment must be maintained throughout the entire growing span for the child. Preliminary studies by the inventors indicate that the growth hormone can be extracted from the medium utilizing minor modifications of the extraction procedures now used for direct extraction of growth hormone from fresh gland tissues. It is estimated that the cost of preparation and extraction will not be greatly different than the processes now utilized. However, the distinct advantage resides in the ability to obtain as much as 20 times more growth hormone in about four weeks time than can be obtained by extraction of one pituitary gland.

ACTH is the hormone elaborated by the anterior pituitary which regulates the growth, development and function of the adrenal cortex of the supra-renal glands which release the corticosteroid group of hormones which are concerned with regulation of protein synthesis, cell replication and growth and regulation of the body's inflammatory response.

The gonadotrophic hormones (FSH, LH, PRL), are concerned with the development, maturation and growth of the male and the female gonads and paragonadal organs like the mammary glands and prostate in terms of their function and hormone synthesis and release. They are also concerned with the function of other organs such as the liver, parts of the brain and the adrenal glands.

TSH regulates the development and control of functions of the thyroid gland which is concerned with development, maturation and rate of function of the cells of the human body.

Whereas at present available supplies of ACTH and TSH are non-human in origin or semi-synthetic, the use of human ACTH and TSH when available is advantageous in terms of greater degree of function and lower antigenicity.

Most of the gonadotrophins used today are placental in origin. Human pituitary gonadotrophins are not easily available or not available in larger amounts and hence have been used only in limited experimental and diagnostic work. The availability of pituitary gonadotrophins especially FSH and LH is not only more advantageous than the placental hormones but the production of appropriate anti-hormones to FSH and LH would enable one to develop newer contraceptives which are being experimented upon. Finally, whereas FSH, LH, ACTH and TSH of animal or semi-synthetic origin can be used in man, only human growth hormone and only human prolactin can be used in man. There is a great demand for human prolactin, almost more so than for human growth hormone, to treat a host of obstetric and gynecological conditions but owing to the total lack of availability on a scale required for clinical treatment, prolactin has not been used on a large scale. Hence, this process, which provides human prolactin, enables the treatment of some obstetric-gynecological conditions.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A nutrient culture medium composition adapted to the production of Prolactin from the pituitary by serial sub-culturing, said composition consisting essentially of amino acid-rich nutrient Medium 199-1X with Earle's modified salts supplemented by the addition of about 5 to 20 ml of liver extract and about 6 to 20 I.U. of insulin per liter of Medium 199-1X, minor amounts of anti-bacterial and anti-fungal agents and about 10 to 100 mg per liter of Medium 199-1X of an aqueous suspension of a substance with progesteron-androgenic activity.

2. A composition according to claim 1 adapted to the production of LH and Prolactin further characterized in that said medium composition includes about 5 to 50 mg of an aqueous suspension of a substance with estrogenic activity per liter of Medium 199-1X.

3. A process for the production of Prolactin which comprises:
    (A) preparing a nutrient amino acid-rich medium composition according to claim 1 in an open aeration incubation vessel,
    (B) dispersing cells of the anterior pituitary in said medium,
    (C) initially growing said cells under aerated cell growth conditions for several days,
    (D) sub-culturing the resulting initial culture and reconstituting the original volume with additional medium,
    (E) growing the sub-culture under aerated cell growth conditions for a further several days,
    (F) serially sub-culturing every several days until the desired optimum growth level is reached, and
    (G) separating the media from the cells and extracting the hormones from the media.

4. A process according to claim 3 for the production of LH and Prolactin further characterized in that said medium composition includes about 5 to 50 mg per liter of Medium 199-1X of an aqueous suspension of a substance with estrogenic activity.

* * * * *